United States Patent [19]

Bilge et al.

[11] Patent Number: 4,711,984

[45] Date of Patent: Dec. 8, 1987

[54] ULTRASONIC METHOD AND APPARATUS FOR SPOT WELD CONTROL

[75] Inventors: Umit Bilge, Clawson; August F. Scarpelli; Ronald E. Schwartz, both of Warren, all of Mich.; John J. Ross, Dunedin, Fla.

[73] Assignee: General Motors Corporation, Detroit, Mich.

[21] Appl. No.: 23,250

[22] Filed: Mar. 9, 1987

[51] Int. Cl.⁴ .................................... B23K 11/24
[52] U.S. Cl. ........................... 219/110; 219/109
[58] Field of Search .............. 219/110, 109, 117.1; 73/597, 598

[56] References Cited

U.S. PATENT DOCUMENTS

| | | | |
|---|---|---|---|
| 3,384,733 | 5/1968 | Burbank et al. | 219/109 |
| 3,410,983 | 11/1968 | Deutsch et al. | 219/109 |
| 3,726,130 | 4/1973 | Hurlebaus | 219/109 |
| 3,810,385 | 5/1974 | McFaul et al. | 73/71.5 U |
| 4,099,045 | 7/1978 | Okuda et al. | 219/109 |
| 4,449,029 | 5/1984 | Nied | 219/110 |
| 4,472,620 | 9/1984 | Nied | 219/110 |
| 4,596,143 | 6/1986 | Norel | 73/598 |

FOREIGN PATENT DOCUMENTS 55-88988  7/1980  Japan ........................... 219/110

OTHER PUBLICATIONS

G. E. Burbank et al, "Ultrasonic In-Process Inspection of Resistance Spot Welds", 4/1966.

A. Stiebel et al, "Monitoring & Control of Spot Weld Operations", 1968.

Primary Examiner—Clifford C. Shaw
Attorney, Agent, or Firm—Warren D. Hill

[57] ABSTRACT

Ultrasonic transducers spring biased into seating engagement in a pair of opposed spot welding tips transmit and receive ultrasonic waves and associated circuitry measures the time of flight between the transducers which is a function of tip separation, workpiece temperature and nugget size which are indicators of the progress of a weld. The rate of change of flight time is measured and the weld current is adjusted early in the weld cycle to maintain a preset rate of weld growth. The weld current is terminated later in the cycle if the transit time rate falls below another preset value. Otherwise the weld current and termination time follow a standard schedule.

5 Claims, 4 Drawing Figures

ULTRASONIC METHOD AND APPARATUS FOR SPOT WELD CONTROL

FIELD OF THE INVENTION

This invention relates to a method and apparatus for controlling resistance spot welds and particularly to such a method and apparatus using ultrasonic transit time measurements which are related to weld progress.

BACKGROUND OF THE INVENTION

Many techniques have been attempted for monitoring or controlling resistance spot welds during the welding operation. These have included sensing weld resistance, acoustic emissions, weld tip displacement, and ultrasonic testing. Very few of the attempts have been commercially successful and any successes have been limited to narrow limits of operation or nearly ideal welding operations. Environments such as automotive manufacture provide less than ideal condition and varied parameters so that different metal thicknesses, number of layers, and metal coatings all challenge the ability of a given approach to weld control.

Ultrasonics have been tried for weld monitoring with no real success prior to this invention. The usual ultrasonic method is to try to track the weld nugget growth by transmitting ultrasonic energy through the weld and analyzing the signal amplitude variations. The patent to Burbank et al U.S. Pat. No. 3,384,733 is an example of this type.

Weld tip displacement has been used to track the progress of a weld and terminate the weld current when the displacement indicates that indentation has occurred. This is shown by Steibel et al, "Monitoring and control of spot Weld Operations", Society of Automotive Engineers, 1986. In that case the only control is the termination time, the current being controlled by a preset schedule.

SUMMARY OF THE INVENTION

It is therefore an object of the invention to provide a method and apparatus for monitoring the progress of a weld and using a feedback control to alter the weld parameters during the weld process.

The invention is carried out by the method of controlling a resistance spot weld comprising the steps of: transmitting ultrasonic pulses between spot weld tips during a weld cycle, measuring the transit time of the ultrasonic pulses to obtain weld nugget growth information, the transit time of each pulse being a function of weld nugget growth, determining the rate of transit time change from the transit times of at least two pulses, comparing the rate of transit time change to a preset range during the early portion of the weld cycle and, when there is a discrepancy, adjusting the weld current to conform the measured rate to the preset range, and comparing the rate of transit time change to a preset rate during a later portion of the weld cycle and, when the measured rate falls below the preset rate, terminating the weld current.

The invention is further carried out by a resistance spot weld control having: means for monitoring weld progress including; a coolant cavity in each tip, an ultrasonic transducer in each tip, spring means for biasing each transducer against the bottom of its respective tip cavity, and circuit means for activating the transducers and periodically measuring the transit time of ultrasonic signals between the transducers; and processor means programmed to store target rate of transit time change values, b) calculate rate of transit time change values from the measured transit times, and c) compare the target values and data values to determine any substantial variation from target rate of transit time change and produce a current change signal to correct for such a variation.

BRIEF DESCRIPTION OF THE DRAWINGS

The above and other advantages of the invention will become more apparent from the following description taken in conjunction with the accompanying drawings wherein like reference numerals refer to like parts and wherein.

DESCRIPTION OF THE PREFERRED EMBODIMENT

It has been found that the transit time of ultrasonic signals between electrode mounted transducers is determined by several parameters. The separation of the electrodes due to the thickness of the workpiece and portions of the electrodes establishes the nominal transit time and further separation changes due to thermal expansion and contraction effects changes in the transit time. More dominant influences in the change of transit time, however, are the effects of temperature and phase on the velocity of the ultrasonic signal. As the temperatures of the workpiece and the electrodes increases the velocity decreases; in addition, the velocity in the molten nugget is much lower than in the solid phase. Thus the rate of heating and melting of the workpiece is directly reflected in changes of the transit time. Thus transit time can be used to monitor the progress of a weld. The rate of change of transit time in the early portion of a weld cycle is useful as a measure of the heating rate and later, when the nugget is forming, is useful as a measure of the nugget growth.

Figure 1:
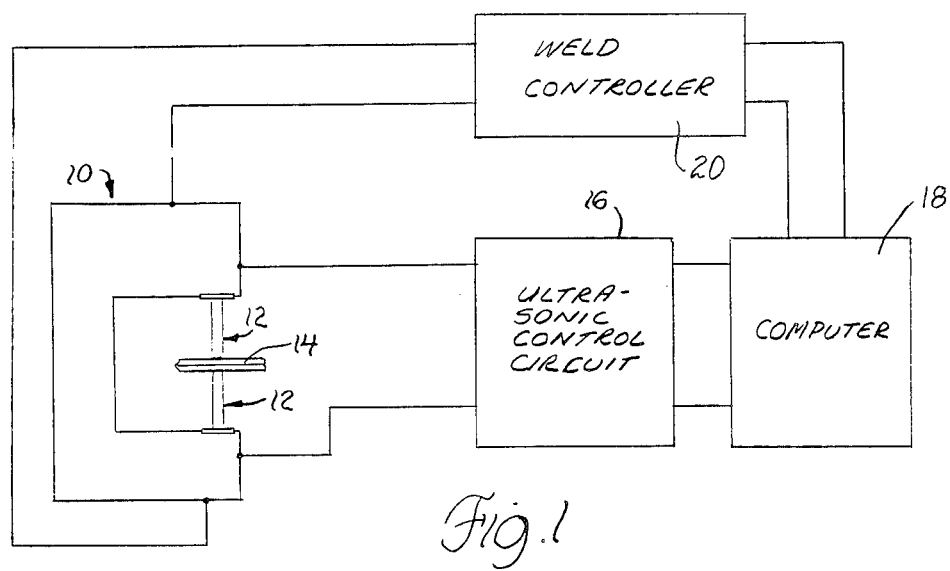
FIG. 1 is a schematic diagram of a weld control apparatus to the invention.
Figure 2:
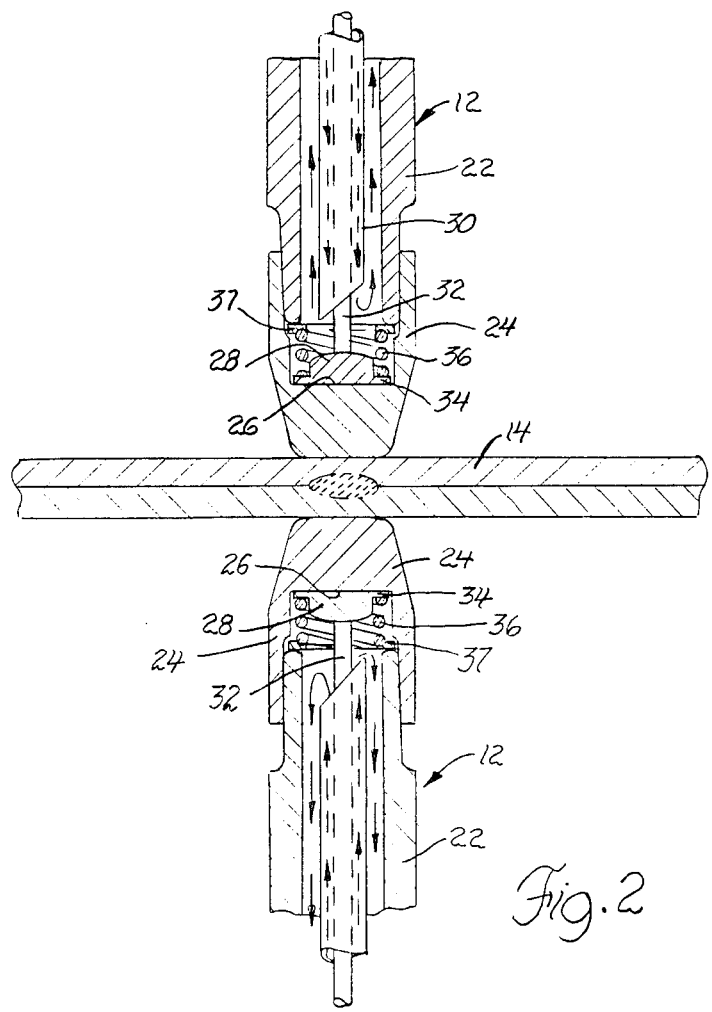
FIG. 2 is a cross-sectional view of welding electrodes for the apparatus of FIG. 1.

Referring to FIGS. 1 and 2, the apparatus for monitoring the progress of a spot weld and controlling the progress in real time comprises a spot welder 10 having electrodes 12 for welding a workpiece 14, an ultrasonic control circuit 16, a computer or other processor 18, and a conventional weld controller 20. The two electrodes are the same and each comprise a shank 22 and a weld tip 24 coupled to the shank by a taper fit. Both elements are hollow to accommodate coolant flow in the conventional manner. The tip 24 differs from the ordinary tip in that the bore terminates in a flat surface 26 to facilitate good seating of an ultrasonic transducer 28. A high temperature couplant in the form of a film of grease between the transducer 28 and surface 26 insures good ultrasonic transmission. A water flow tube 30 within the shank 22 carries cooling water into the tip and also provides a passage for the transducer cable 32 which carries a driving signal to or a received signal from the transducer 28. Alternatively, the cable may be routed between the tube 30 and the shank 22 and out through a port, not shown, in the side of the shank. The transducer 28 is hat-shaped with a radial flange 34. A coil spring 36, compressed between the end of the shank 22 and the transducer 28, surrounds the crown of the hat and one end presses against the flange 34 to urge the transducer 28 into firm contact with the tip surface 26. The other end of the spring is soldered to a washer 37 which bears against the end of the shank.

The weld tip/transducer assembly has two important advantages arising from the spring arrangement. First, the spring assures that the transducer makes good contact with the surface 26 so that the ultrasonic signal will be effectively transferred to or from the tip. Prior attempts at instrumenting weld tips for ultrasonics included bonding the transducer to the inner surface of the tip. Such bonding proved to be temporary since the transducers came loose during the rigorous welding process. Moreover, the transducer, if bonded to the tip must be discarded when the tip is replaced. Since tip life is short, that practice would be economically prohibitive. Second, when the transducer is spring biased against the tip, replacement of the tip is easy and, in fact, is essentially the same as replacing a conventional non-instrumented tip: the tip is simply knocked off the shank and a new one is installed with a dab of couplant grease applied to the transducer. The transducer will automatically be spring biased against the surface 26 of the new tip.

In operation of the apparatus the ultrasonic control circuit 16 energizes one of the transducers with frequency bursts at the rate of 1000 to 3000 times per second. The energizing frequency is determined by the transducer crystal frequency which is about 5 MHz but may be in the range of 0.1 MHz to 15 MHz. The ultrasonic signal is transmitted to the other transducer and the time of flight (or transit time) is measured by the circuit 16. Any change in temperature, tip spacing or nugget size will change the transit time accordingly so that weld progress is instantly and accurately measured. The transit time is then sampled by the computer 18 once each half-cycle for analysis by comparison of differences in transit time to programmed target values according to the method to be described, and the computer, in turn, signals to the weld controller 20 any change in the weld schedule needed to optimize the weld process.

Traditionally, the weld controller 20 predetermines a weld current schedule to provide energy for nugget formation at a given rate intended to be the optimum rate for a given weld and also sets a termination time. The exact conditions encountered during a particular weld may differ from the ideal due to poor part fit-up, electrode wear, or other variables. To achieve adaptive control, the method of the invention uses the time of flight information to monitor the progress of the weld, compare the progress to an optimal model, and modify the scheduled current and termination time, if required, to form an acceptable weld. The preferred practice is to make one transit time measurement for each half-cycle but multiple measurements in each half-cycle may be made and averaged.

Figure 3:
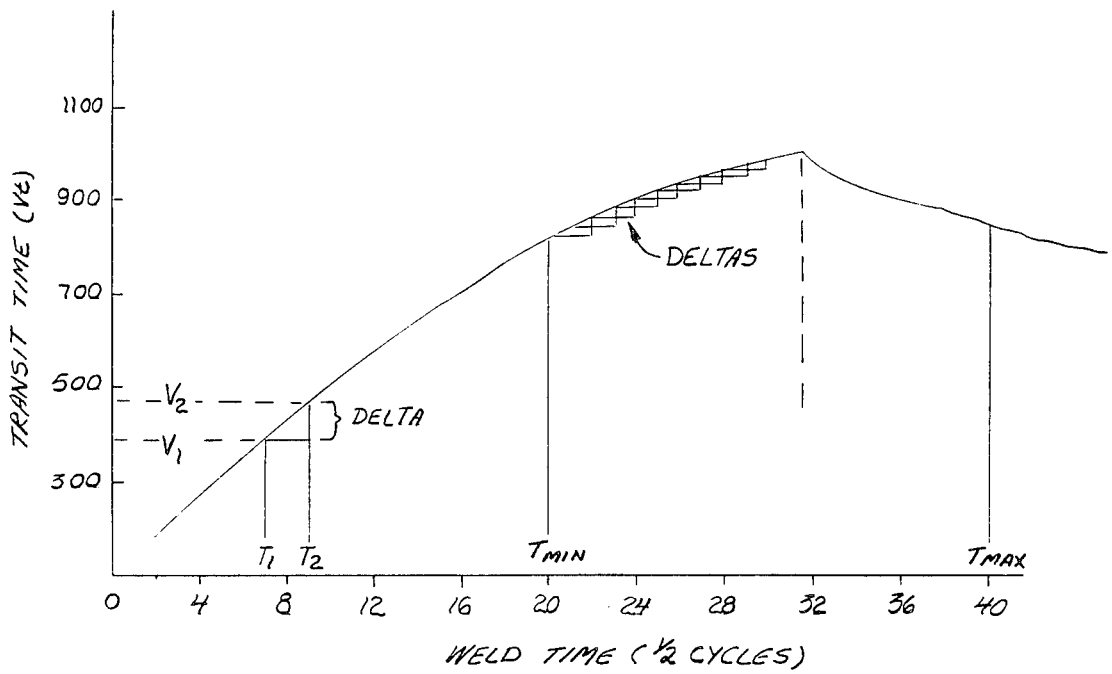
FIGS. 3 and 4 are graphs of the profile of transit times during welds on two different workpieces and illustrating the application of a control algorithm according to the invention.

The heating rate of the workpiece as reflected in the transit time rate of change is accurately determined and must be within prescribed limits in order to form an acceptable weld nugget within the allotted time. The weld duration is truncated if the transit time information indicates that the nugget growth in the line of travel of the signal has slowed to a preset rate. FIG. 3 shows the transit time profile for a weld between two sheets of bare steel. The Y-axis is transit time expressed in arbitrary units Vt and the X-axis is weld time expressed as current half-cycles. The slope at any point on the rising curve indicates the rate of change of transit time and is measured by the difference in transit time (Delta) over a full cycle.

During an early portion of the weld cycle a time increment is defined by T1 and T2 when Delta is measured to determine whether the slope (rate of heating) is proper. If Delta is below a minimum (DeltaMin) the current is increased and if Delta is above a maximum (DeltaMax) the current is decreased to compensate for the discrepancy. Later in the weld cycle when the weld might be expected to be completed, a pair of limits (Tmin and Tmax) are set and Delta is measured in every half-cycle in that range and compared to a value (DeltaEnd) which indicates that the nugget growth has slowed to a value which indicates that the weld is complete. Then the current is terminated. If the DeltaEnd is not found the current will be terminated at Tmax by the controller.

The method can be described by the algorithm which forms the basis for programming the computer 18:
Start weld at StartHeat:
Record Vt at T1 and T2:
Delta=V2−V1:
If Delta < DeltaMin increase heat:
If Delta > DeltaMax decrease heat:
After Tmin determine Delta for each half-cycle:
If Delta < DeltaEnd stop the weld current:
If Tmax is reached stop the weld current.

For the particular case illustrated in FIG. 3 the workpiece was two sheets of bare steel having thicknesses of 0.073 and 0.044 inch respectively. The parameters for the algorithm were:

| | |
|---|---|
| StartHeat | 30% |
| T1 | 7 half-cycles |
| T2 | 9 half-cycles |
| Tmin | 20 half-cycles |
| Tmax | 40 half-cycles |
| DeltaMin | 80 units |
| DeltaMax | 100 units |
| DeltaEnd | 56 units |

As can be seen from the graph the Delta was within the prescribed limits or target range and the current was not adjusted. The second target value, DeltaEnd, was passed at half-cycle 32 and the current stopped.

Figure 4:
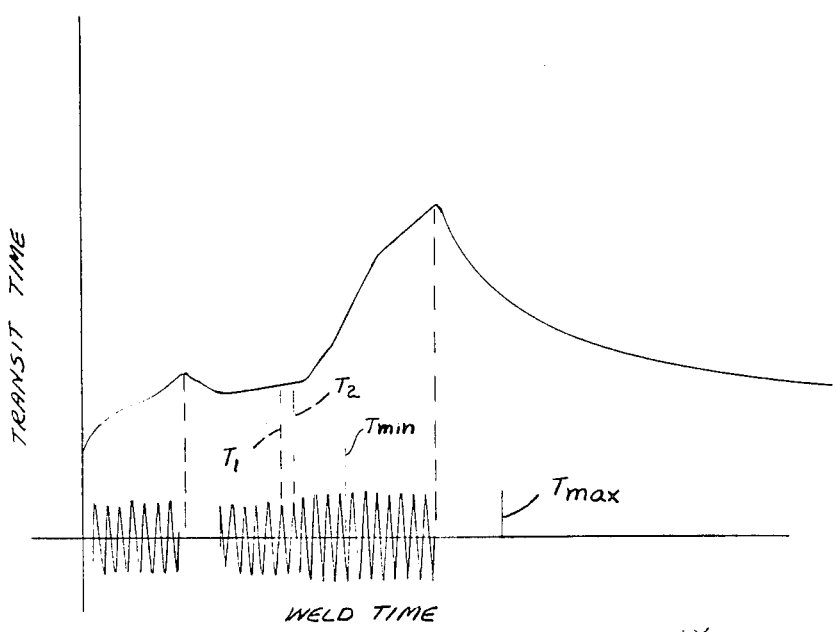

Another example is shown in FIG. 4 for a workpiece comprising two galvanized sheets each having a thickness of 0.052 inch. The weld controller is set to provide welding current in two stages separated by a cooling period. The transit time profile shows the workpiece heating and cooling as the current is applied or not. The current waveforms are superimposed on the graph to show each stage. In this case the heating rate was quite low when sampled at T1-T2 so that the Delta was below DeltaMin. The current was increased resulting in larger waveform amplitudes and an increased slope of the profile. As Delta sampling resumed after Tmin, a decreasing slope near the peak allowed the detection of a Delta below DeltaEnd to terminate the current. The half-cycles are numbered according to the actual count of current pulses so that the number does not continue to increment during the cooling period. The algorithm given above is directly applicable to this weld schedule and the parameters were as follows:

| | |
|---|---|
| StartHeat | 40% |
| T1 | 23 half-cycles |
| T2 | 25 half-cycles |
| Tmin | 18 cycles |
| Tmax | 30 cycles |
| DeltaMin | 55 units |
| DeltaMax | 100 units |
| DeltaEnd | 56 units |

A particular advantage of this control is that it terminates current at or near the optimum weld strength when the nugget becomes so large that its growth in the region directly between the electrodes becomes slow. This is in contrast to those methods which are able to only recognize a large change in workpiece thickness which occurs at metal expulsion. The expulsion sensing systems can provide useful weld control on the basis that expulsion is indicative of a strong or good weld. However it is generally recognized that the weld has passed its peak strength by the time expulsion occurs so that an earlier detection can result in even stronger welds. Moreover, the splash of molten metal which can accompany expulsion is avoided. Repeated testing of this method and apparatus under varying conditions and for different types of welds and two or more sheets in the workpiece has yielded acceptable welds. The computer control can be readily adapted to scheduling for multiple welds of differing types with the proper parameters programmed for each weld.

It will thus be seen that the invention provides a practical way of accurately tracking weld progress and controlling weld parameters in real time to assure acceptable welds.

The embodiments of the invention in which an exclusive property or privilege is claimed are defined as follows:

1. The method of controlling a resistance spot weld comprising the steps of:
   transmitting ultrasonic pulses between spot weld tips during a weld cycle,
   measuring the transit time of the ultrasonic pulses to obtain weld progress information, the transit time of each pulse being a function of temperature and nugget growth,
   determining the rate of change of transit time from the transit times of at least two pulses,
   comparing the rate of change of transit time to a preset range during the early portion of the weld cycle and, when there is a discrepancy, adjusting the weld current to conform the measured rate to the preset range, and
   comparing the rate of change of transit time to a preset rate during a later portion of the weld cycle and, when the measured rate falls below the preset rate, terminating the weld current.

2. The method of controlling a resistance spot weld comprising the steps of:
   transmitting ultrasonic pulses between spot weld tips during a weld cycle,
   measuring the transit time of the ultrasonic pulses to obtain weld progress information, the transit time of each pulse being a function of temperature and nugget growth,
   determining the rate of change of transit time from the transit times of at least two pulses,
   comparing the rate of change of transit time to a preset range during the early portion of the weld cycle and increasing the weld current when the measured rate is below the preset range and decreasing the current when the measured rate is above the preset range, and
   comparing the rate of change of transit time to a preset rate during a later portion of the weld cycle and, when the measured rate falls below the preset rate, terminating the weld current.

3. The method of controlling a resistance spot weld comprising the steps of:
   initiating a weld cycle according to an established weld current schedule,
   transmitting ultrasonic pulses between spot weld tips during the weld cycle,
   measuring the transit time of the ultrasonic pulses to obtain weld progress information, the transit time of each pulse being a function of temperature and nugget growth,
   determining the rate of change of transit time from the transit times of at least two pulses,
   comparing the rate of change of transit time to a preset range during the early portion of the weld cycle and, when there is a discrepancy, overriding the established weld current schedule by adjusting the weld current in a sense to compensate for the discrepancy, and
   comparing the rate of change of transit time to a preset rate during a later portion of the weld cycle and, when the measured rate falls below the preset rate, overriding the established weld current schedule by terminating the weld current.

4. In a resistance spot weld control:
   means for monitoring weld growth progress including;
   a coolant cavity in each tip,
   an ultrasonic transducer in each tip,
   spring means for biasing each transducer against the bottom of its respective tip cavity, and
   circuit means for activating the transducers and periodically measuring the transit time of ultrasonic signals between the transducers; and
   processor means programmed to
   (a) store target rate of change of transit time values,
   (b) calculate rate of change of transit time data values from the measured transit times, and
   (c) compare the target values and data values to determine any substantial variation from target rate of change of transit time and produce a current change signal to correct for such a variation.

5. In a resistance spot weld apparatus including a pair of opposed weld electrodes:
   each electrode comprising a shank and a tip which fits over the cap and having a coolant cavity in the shank and tip,
   means for monitoring weld growth progress including;
   an ultrasonic transducer in each tip seated in the bottom of the tip cavity, coil spring means compressed between the end of the shank and the transducer for biasing each transducer against the bottom of its respective tip cavity, and
   circuit means for activating the transducers and periodically measuring the transit time of ultrasonic signals between the transducers; and
   a computer programmed to
   (a) store first and second target rate of change of transit time values, (b) calculate first and second rate of change of transit time data values from the measured transit times, (c) compare the first target values and data values to determine any substantial variation from target rate of change of transit time and produce a current change signal to correct for such a variation, and (d) compare the second target values and data values to determine whether the second data value falls below the second target value and produce a current termination signal, and a weld controller responsive to the signals produced by the computer for adjusting weld current and terminating the weld.

* * * * *